US010506149B2

(12) United States Patent
Wolf et al.

(10) Patent No.: US 10,506,149 B2
(45) Date of Patent: Dec. 10, 2019

(54) ENDOSCOPE DEVICE FOR AN AUTOMATIC EXAMINATION

(71) Applicant: ZF Friedrichshafen AG, Friedrichshafen (DE)

(72) Inventors: Daniel Wolf, Friedrichshafen (DE); Johannes Schäfer, Friedrichshafen (DE); Marton Kurucz, Friedrichshafen (DE)

(73) Assignee: ZF Friedrichshafen AG, Friedrichshafen (DE)

( * ) Notice: Subject to any disclaimer, the term of this patent is extended or adjusted under 35 U.S.C. 154(b) by 0 days.

(21) Appl. No.: 16/094,934

(22) PCT Filed: Mar. 22, 2017

(86) PCT No.: PCT/EP2017/056852
§ 371 (c)(1),
(2) Date: Oct. 19, 2018

(87) PCT Pub. No.: WO2017/182222
PCT Pub. Date: Oct. 26, 2017

(65) Prior Publication Data
US 2019/0124250 A1     Apr. 25, 2019

(30) Foreign Application Priority Data

Apr. 21, 2016 (DE) .................. 10 2016 206 810

(51) Int. Cl.
*H04N 5/232* (2006.01)
*A61B 1/00* (2006.01)
(Continued)

(52) U.S. Cl.
CPC ....... *H04N 5/23203* (2013.01); *A61B 1/0008* (2013.01); *A61B 1/126* (2013.01);
(Continued)

(58) Field of Classification Search
None
See application file for complete search history.

(56) References Cited

U.S. PATENT DOCUMENTS 8,753,082 B2   6/2014  Fuglsang-Petersen et al.
9,699,417 B2*  7/2017  Bousquet ............... G01N 21/91
(Continued)

FOREIGN PATENT DOCUMENTS

DE        198 06 279 A1   12/1998
DE   10 2007 037 542 A1    2/2009
(Continued)

OTHER PUBLICATIONS

German Search Report Corresponding to 10 2016 206 8105 dated Jan. 27, 2017.
(Continued)

*Primary Examiner* — Kate H Luo
(74) *Attorney, Agent, or Firm* — Davis & Bujold PLLC; Michael J. Bujold

(57) ABSTRACT

An endoscope device for the automated inspection of the interior of a transmission. The endoscope has a control unit and an evaluation unit, a feed unit having a swivel element, a changer magazine having a plurality of guide channels and an endoscope. The control unit is connected to the endoscope and is largely provided for controlling the endoscope and for transmitting images to the evaluation unit. The swivel element is provided for aligning a distal end of the endoscope with respect to a relevant guide channel, and the feed unit is provided for axially passing the endoscope through the relevant guide channel. Furthermore, a transmission, in particular for a wind turbine, has a transmission housing having at least one access opening for receiving an endoscope device. Automated inspection of the interior of the transmission can be conducted by the endoscope device.

11 Claims, 2 Drawing Sheets

(51) Int. Cl.
*A61B 1/12* (2006.01)
*H04N 5/225* (2006.01)
*F03D 17/00* (2016.01)

(52) U.S. Cl.
CPC ........... *F03D 17/00* (2016.05); *H04N 5/2256* (2013.01); *H04N 2005/2255* (2013.01)

(56) References Cited

U.S. PATENT DOCUMENTS

| | | | |
|---|---|---|---|
| 2012/0312103 A1* | 12/2012 | Hannott | A61B 1/0056 73/865.8 |
| 2015/0036150 A1 | 2/2015 | Kobayashi et al. | |
| 2016/0194088 A1* | 7/2016 | Leutard | F01D 21/003 415/118 |
| 2017/0006201 A1* | 1/2017 | Segura | G01N 29/14 |
| 2017/0074120 A1* | 3/2017 | Drouin | F01D 21/003 |

FOREIGN PATENT DOCUMENTS

| | | |
|---|---|---|
| DE | 10 2009 032 667 A1 | 1/2011 |
| JP | S62-266458 A | 11/1987 |
| JP | 2000-089131 A | 3/2000 |
| JP | 2005-323778 A | 11/2005 |
| JP | 2006-014959 A | 1/2006 |
| JP | 2008-224727 A | 9/2008 |

OTHER PUBLICATIONS

International Search Report Corresponding to PCT/EP2017/056852 dated Sep. 13, 2017.
Written Opinion Corresponding to PCT/EP2017/056852 dated Sep. 13, 2017.

* cited by examiner

ENDOSCOPE DEVICE FOR AN AUTOMATIC EXAMINATION

This application is a National Stage completion of PCT/EP2017/056852 filed Mar. 22, 2017, which claims priority from German patent application serial no. 10 2016 206 810.5 filed Apr. 21, 2016.

FIELD OF THE INVENTION

The invention relates to an endoscope device for the automated inspection of the inside of a transmission, wherein the endoscope device can be used in particular in a transmission of a wind turbine.

BACKGROUND OF THE INVENTION

To inspect transmissions, an image of the inside of a transmission is necessary. To obtain this view, the physical presence of service personnel is usually required at the transmission. To prevent a complicated disassembly of the transmission, endoscopes for examining the interior of the transmission can be manually introduced via inspection openings. This is time-consuming and expensive, in particular for transmissions of wind turbines.

DE 10 2009 032 667 A1 discloses a transmission of a wind turbine, wherein the transmission has a transmission housing. At least one access opening for introducing an implement into the transmission housing is provided on the outside of the transmission housing. At least one guiding means for the implement is provided in the interior of the transmission housing, such that the implement can be moved and/or positioned within the guiding means. Parts of the transmission in the transmission housing are checked and/or attended to by means of the drive implement introduced into the guide. In particular, at least one physical property of a medium, in particular oil, in the transmission housing, or physical properties of components of the transmission, are detected.

SUMMARY OF THE INVENTION

The object of the present invention is to provide an endoscope device for automated inspection of the interior of a transmission.

This problem is solved by the subject matter of the independent claims. Preferred embodiments are the subject matter of the dependent claims.

The endoscope device according to the invention for automated inspection of the interior of a transmission comprises a control unit and an evaluation unit, a feed unit having a swivel element, a changer magazine having a plurality guide channels and an endoscope, wherein the control unit is connected to the endoscope and is provided largely for controlling the endoscope and for forwarding images to the evaluation unit, wherein the swivel element is provided for aligning a distal end of the endoscope with respect to a relevant guide channel, and wherein the feed unit is provided for axial passage of the endoscope through the relevant guide channel. In other words, the endoscope device permits a remote view of the interior of the transmission. The endoscope device is preferably controlled via operator controls provided for this purpose, in particular via a web interface. An automated inspection shall be understood to denote an at least partially automated inspection. In other words, at least the physical presence of maintenance personnel on the transmission is not required because the endoscope device is operated automatically. In particular, for this purpose the control unit can be controlled via a terminal, preferably by a computer system. A computer system shall be understood as a device consisting of physical components, the so-called hardware, and programs interacting therewith, the so-called software. The computer system is advantageously designed as a computer or as a smartphone and controlled either by maintenance personnel or a program. In the case of fully automated control, both the inspection and the evaluation and summary of the inspection are conducted without the intervention of the maintenance personnel.

The transmission comprises a transmission housing, which has at least one access opening for receiving the endoscope device, wherein an automated inspection of the interior of the transmission can be conducted by means of the endoscope device. Thus, the endoscope device is integrated in the transmission. The control unit is preferably connected wirelessly to the evaluation unit, wherein the evaluation unit is disposed outside of the transmission. In particular, the control unit controls not only the endoscope, in particular the viewing angle in the interior of the transmission, but also an infeed on the feed unit and an angle on the swivel element, which is provided for selecting the respective guide channel. Furthermore, the changer magazine is arranged in or on the access opening and preferably replaces an inspection opening. A guide channel in the changer magazine is connected to an inspection channel or a rail in the transmission housing, which is intended to guide the endoscope to the position to be inspected, in particular a gear, a shaft or a bearing. Consequently, the changer magazine can be used to reroute the endoscope between the respective inspection channels or rails in an automated manner. Preferably, infeed, rotation and adjustment of the distal end of the endoscope are power-adjustable. The control unit is designed to function either locally or remotely and preferably communicates with a telemetry unit in the endoscope using signal technology.

Preferably, at least one guide channel is connected to a cleaning device in order to clean at least the distal end of the endoscope. The cleaning device comprises a cleaning agent, which is provided for cleaning the endoscope, in particular to remove transmission oil. Furthermore, the cleaning device may in addition comprise brush elements, a flushing device, an ultrasonic bath or a cleaning cassette. Preferably, the endoscope is dried while being pulled out of the cleaning device. A compressed air device or a stripping means, in particular made of a rubber, a textile or a porous material, is provided for this purpose in particular.

The endoscope preferably has a camera device (image sensor) at the distal end. The camera device is intended for digital image acquisition and generates high-resolution photo or video recordings of the interior of the transmission. Alternatively, it is also conceivable that the endoscope has different optical elements, in particular lenses and mirrors, in order to transmit an acquired image from the interior of the transmission to the control device. Furthermore, the camera device can also be contained in the control device, in which case a fiber optic cable is connected to the distal end of the endoscope.

Furthermore, the endoscope preferably has an illumination device at its distal end. The illumination device is provided for illuminating the interior of the transmission and comprises at least one LED. In particular, the illumination device can be provided both for generating a photoflash and for permanent illumination. The photoflash is used in particular for the brief illumination of the interior of the transmission while a photo is taken. Furthermore, the camera device is advantageously provided for photographing or video recording in the dark, and comprises at least one infrared sensor or a night vision camera. Photographs or video recordings can be made on demand at regular or irregular intervals. Preferably, the camera device interacts with at least one sensor element for condition monitoring of a transmission element, wherein the camera device starts taking photos or recording videos of the relevant transmission element in the case of a critical signal from the at least one sensor element. Consequently, an event-controlled photo-taking or video-recording is conceivable.

A critical signal shall be understood in particular to denote the deviation of a state variable from an expected value or from an expected value range. This deviation can have different causes. An example of such a deviation is a vibration change due to growing cracks in transmission components, such as shafts. The output of a critical signal thus indicates a discrepancy or an error of the transmission element to be monitored. Upon the output of a critical signal, necessary measures can be initiated after a visual check by means of the endoscope device. In other words, the endoscope device permits an automated remote view of the transmission interior.

Further preferably, the guide channels in the changer magazine are at least partially adjacent to one another, along an arc or a line. Preferably, the guide channels are formed in a plane and are arranged identical to a revolver magazine, i.e. circular and thus rotationally symmetrical. Furthermore, it is also conceivable to arrange the guide channels linearly adjacent to one another or to form a matrix of columns and rows of guide channels. A three-dimensional design of the changer magazine, in particular a spherical or spherical segment-shaped configuration is also conceivable.

According to a preferred embodiment, the relevant guide channel has a sensor for detecting the position of the endoscope. The exact position of the distal end of the endoscope can be determined by means of the sensor. In an advantageous development, the control unit of the endoscope device and a control unit of the transmission are connected to one another in such a way that different positions within the transmission can be accessed. For instance, a comparison of the speed of a gear can be used to detect and assign the individual teeth of a gear.

The transmission itself may also have guide channels or guide rails. These guide channels in the transmission lead to the points to be inspected. The guide channels, which bridge rotating components, may also be aligned. In a state, in which movable parts of the transmission are coupled to each other by the endoscope device (for an inspection), it has to be ensured that the transmission is immobile. Otherwise, damage to the endoscope device would result. Here, too, it would be expedient if the control unit of the endoscope device and the control unit of the transmission are in communication with each other, or data are exchanged.

In particular, the evaluation unit is provided for generating a virtual model of the interior of the transmission. In this way, real images can be combined to form a virtual model in order to enable a 360° view inside the transmission. Furthermore, images can be superimposed, in particular current real images on virtual model images. Real images and model images can be compared therein. Furthermore, additional information, such as part numbers and/or virtually numbered teeth of gears can be displayed and form part of the operating concept. In particular, the endoscope can specifically approach a tooth flank of a defined tooth and findings can be compared to archived images of that tooth.

For this purpose, in particular a position sensor is provided on the relevant toothing or shaft to permit the relevant tooth to be found again. In particular, the control device of the endoscope device is connected to a control device of the transmission or to the respective sensor elements of the transmission, in particular sensors for determining the position and for determining the angle of rotation. Due to the signaling connection between the control device of the endoscope device and the control device of the transmission, guides between moving parts are synchronized. While the endoscope couples movable parts, in particular bridges two relatively movable parts, the transmission is not moved.

Preferably, the evaluation unit is provided for the automated evaluation of the acquired images. For this purpose, in particular the images are compared to reference images of a database, wherein the reference images show all known or previously occurred damage or critical changes. This evaluation can in particular be associated with operational management systems, which can initiate an inspection, for example due to condition monitoring abnormalities, in an automated manner. Depending on the degree of automation and the result of the inspection, follow-up measures, such as the replacement of parts, can be instigated or the operation of the transmission can be changed.

BRIEF DESCRIPTION OF THE DRAWINGS

Embodiments of the invention with reference to the drawings, in which the same or similar elements are provided with the same reference numerals, will be explained in more detail below. In the figures

DETAILED DESCRIPTION OF THE PREFERRED EMBODIMENTS

Figure 1:
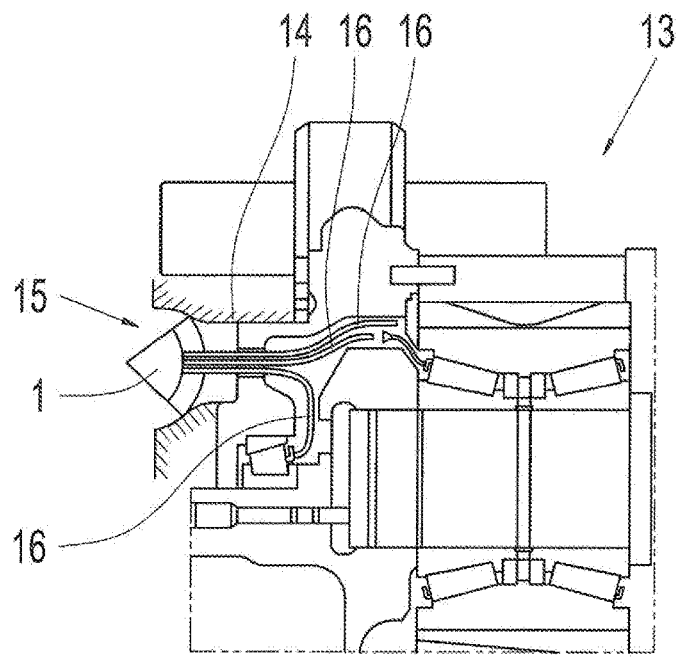
FIG. 1 shows a simplified schematic sectional view of a partially shown transmission having an endoscope device according to the invention for the automated inspection of the interior of a transmission.

According to FIG. 1, a transmission 13 according to the invention for a wind turbine has a transmission housing 14, which comprises an access opening 15. An endoscope device 1 according to the invention is arranged in the access opening 15, wherein an automated inspection of the interior of a transmission can be carried out by means of the endoscope device 1. The transmission 13 has a plurality of guide channels 7 and guide rails 16 for examining various transmission components, in particular different bearing elements, rolling elements, shafts and teeth, which permit the endoscope 8 of the endoscope device 1 to be guided through to the relevant transmission component.

Figure 2:
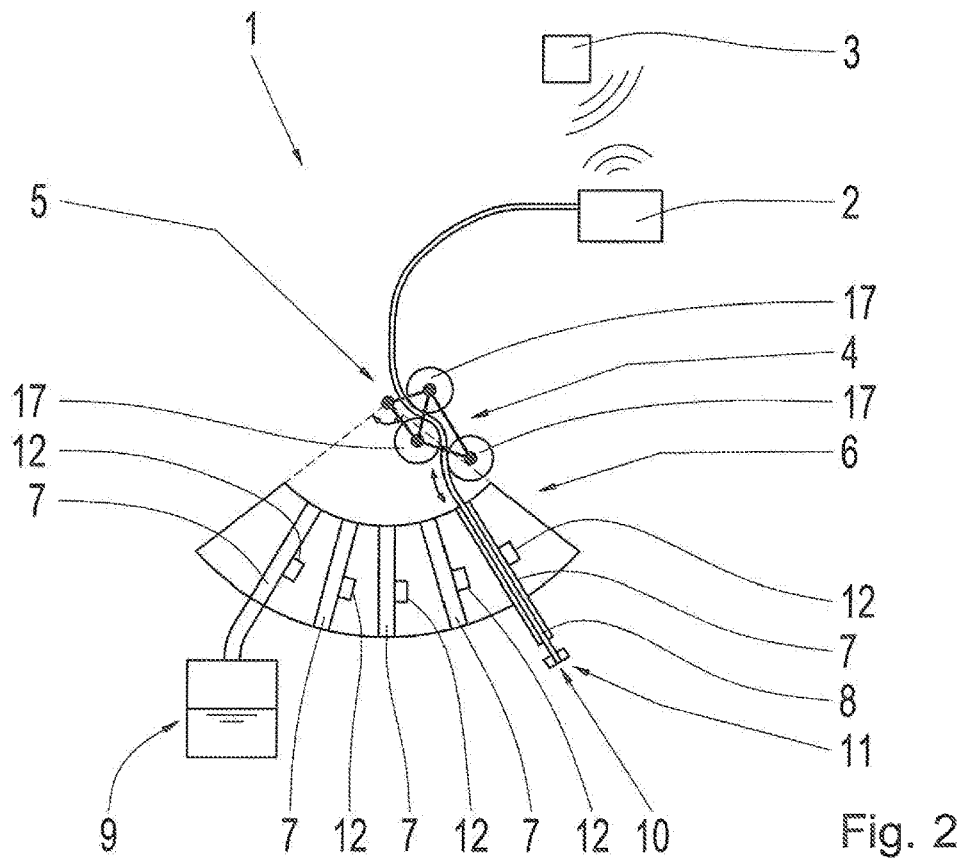
FIG. 2 shows a simplified schematic sectional view of the endoscope device according to the invention of FIG. 1 having a changer magazine according to a preferred exemplary embodiment.

According to FIG. 2, the endoscope device 1 according to the invention of FIG. 1 comprises a control unit 2, a feed unit 4 having a swivel element 5, a changer magazine 6 having a plurality of guide channels 7 and the endoscope 8. Furthermore, the endoscope device 1 also comprises an evaluation unit 3 which is located outside the transmission 13 and which interacts wirelessly with the control unit 2. In particular, the evaluation unit 3 is provided for generating a virtual model of the interior of the transmission, wherein several images are superimposed to form a virtual model for this purpose. Furthermore, the evaluation unit 3 is also provided for the automated evaluation of the acquired images.

The control unit 2 is connected to the endoscope 8 and provided essentially for controlling the endoscope 8 and for forwarding images to the evaluation unit 3. In particular, the endoscope 8 is directly connected to the control unit 2. The swivel element 5 is provided for aligning a distal end of the endoscope 8 with respect to an individual guide channel 7 and thus for selecting the individual guide channel 7. The changer magazine 6 has a plurality of guide channels 7, wherein a guide channel 7 is connected to a cleaning device 9 in order to clean the distal end of the endoscope 8. The changing magazine 6 has a plurality of guide channels 7, wherein a guide channel 7 is connected to a cleaning device 9 in order to clean the distal end of the endoscope 8. Furthermore, the individual guide channel 7 has a sensor 12 for detecting the position of the endoscope 8. The feed unit 4 is provided for axial passage of the endoscope 8 through the individual guide channel 7 to the respective transmission component and has three guide rollers 17, which come to rest against the endoscope 8. The swivel element 5 is designed as a rotatable bearing point of the feed unit 4 and allows swiveling of the feed unit 4 around a swivel axis. Depending on the angular position of the swivel element 5, the distal end of the endoscope 8 is positioned relative to the respective guide channel 7. The endoscope 8 has a camera device 10 and an illumination device 11 at its distal end.

Figure 3:
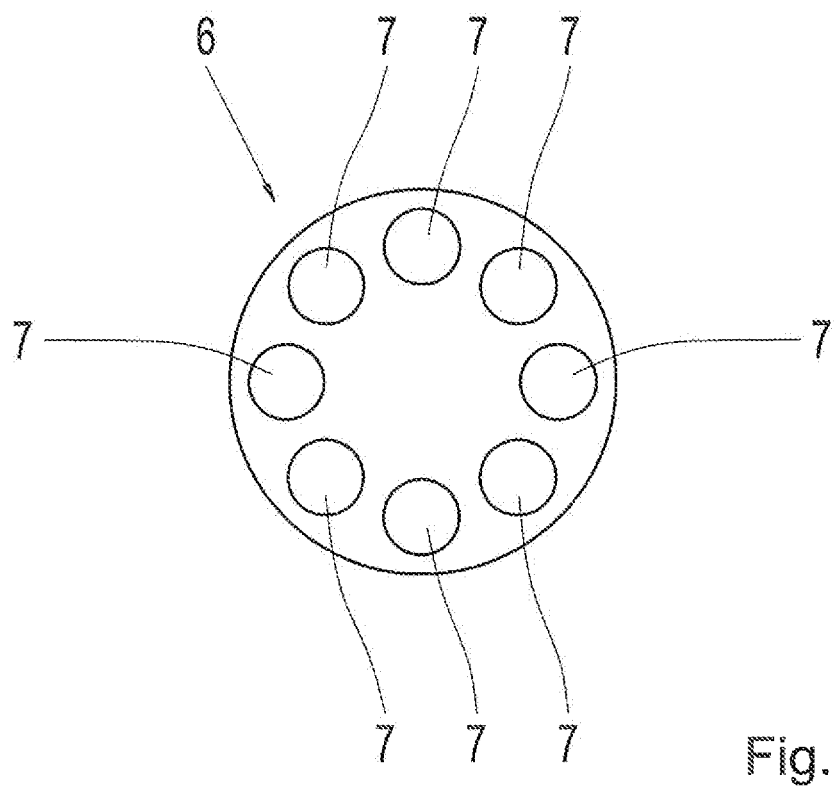
FIG. 3 shows a simplified schematic plan view of a changer magazine according to the invention in accordance with a second embodiment.

FIG. 3 shows an alternative embodiment of the changing magazine 6. The respective guide channels 7 are arranged in a circular manner in the changer magazine 6, wherein the changer magazine 6 is formed rotationally symmetrical.

Figure 4:
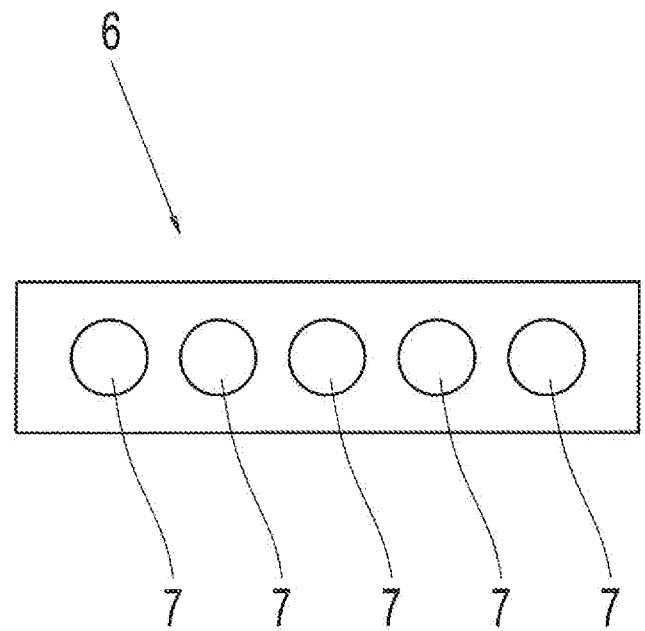
FIG. 4 shows a simplified schematic plan view of a changer magazine according to the invention in accordance with a third embodiment.

FIG. 4 shows an alternative embodiment of the changing magazine 6. There the respective guide channels 7 are arranged linearly adjacent to each other in the changer magazine 6.

REFERENCE NUMERALS 1 sensor device
2 control unit
3 evaluation unit
4 feed unit
5 swivel element
6 changer magazine
7 guide channel
8 endoscope
9 cleaning device
10 camera device
11 illumination device
12 sensor
13 transmission
14 transmission housing
15 access opening
16 guide rail
17 guide roller

The invention claimed is:
1. An endoscope device for automated inspection of an interior of a transmission, the endoscope device comprising:
a control unit,
an evaluation unit,
a feed unit having a swivel element,
a changer magazine having a plurality of guide channels, and
an endoscope,
the control unit being connected to the endoscope and being largely provided for controlling the endoscope and transmitting images to the evaluation unit,
the swivel element being provided for aligning a distal end of the endoscope with respect to a relevant one of the plurality of guide channels, and
the feed unit being provided for axially passing the endoscope through the relevant one of the plurality of guide channels.

2. The endoscope device according to claim 1, wherein the relevant one of the plurality of guide channels is connected to a cleaning device to clean at least the distal end of the endoscope.

3. The endoscope device according to claim 1, wherein the endoscope has a camera device located at the distal end thereof.

4. The endoscope device according to claim 1, wherein the endoscope has an illumination device located at the distal end thereof.

5. The endoscope device according to claim 1, wherein the plurality of guide channels in the changer magazine are arranged at least partially adjacent to one another either along an arc or a line.

6. The endoscope device according to claim 1, wherein the relevant one of the plurality of guide channels has a sensor for detecting a position of the endoscope.

7. The endoscope device according to claim 1, wherein the evaluation unit is provided for generating a virtual model of the interior of the transmission.

8. The endoscope device according to claim 1, wherein the evaluation unit is provided for automated evaluation of acquired images.

9. The endoscope device according to claim 1, wherein the endoscope device is arranged in a transmission of a wind turbine.

10. A transmission for a wind turbine, the transmission comprising:
a transmission housing having at least one access opening for receiving an endoscope device comprising:
a control unit,
an evaluation unit,
a feed unit having a swivel element,
a changer magazine having a plurality of guide channels, and
an endoscope,
the control unit being connected to the endoscope and being provided for controlling operation of the endoscope and transmitting images to the evaluation unit,
the swivel element being provided for aligning a distal end of the endoscope with respect to a relevant one of the plurality of guide channels, and
the feed unit being provided for axially passing the endoscope through the relevant one of the plurality of guide channels so that an automated inspection of an interior of the transmission may be conducted by the endoscope device.

11. An endoscope device for automated inspection of an interior of a transmission of a wind turbine, the endoscope device comprising:
a control unit being connected to an endoscope for controlling operation of the endoscope, the control unit receiving images captured by the endoscope, the control unit being connectable to an evaluation unit which communicates with the control device and receives the images captured by the endoscope and transmitted by the control device;

a feed unit being arranged at an access opening in a housing of the transmission and supporting the endoscope, the feed unit having a swivel element that forms a rotatable bearing point and facilitates swiveling of the feed unit about a swivel axis with respect to the housing of the transmission;

a changer magazine being received within the access opening in the housing and having a plurality of guide channels extending therethrough from an exterior side of the changer magazine and the housing to an interior side of the charger magazine and the interior of the housing;

the swivel element being actuatable to swiveling the feed unit such that a distal end of the endoscope aligns with a selected one of the plurality of guide channels; and the feed unit being actuatable to feed the endoscope through the selected one of the plurality of guide channels from the exterior side of the changer magazine and the housing to the interior side of the charger magazine and the interior of the housing, and each plurality of guide channels being aligned with a different position in the interior of the housing.

* * * * *